United States Patent [19]
Kim

[11] Patent Number: 5,470,746
[45] Date of Patent: Nov. 28, 1995

[54] PICKLED VEGETABLES FERMENTATION DETECTING DEVICE

[75] Inventor: Jae I. Kim, Seoul, Rep. of Korea

[73] Assignee: SamSung Electronics Co., Ltd., Suwon, Rep. of Korea

[21] Appl. No.: 100,340

[22] Filed: Aug. 2, 1993

Related U.S. Application Data

[63] Continuation of Ser. No. 451,565, Dec. 18, 1989, abandoned.

[30] Foreign Application Priority Data

Dec. 30, 1988 [KR] Rep. of Korea ............... 1988/17993

[51] Int. Cl.$^6$ .................................................. C12M 1/34
[52] U.S. Cl. ................. 435/287.1; 435/807; 435/808; 435/296.1; 435/289.1; 435/288.7; 73/19.1; 99/493
[58] Field of Search ...................... 435/3, 29, 30, 435/32, 287, 289, 290, 291, 313, 807, 808; 73/19.04, 19.05, 19.1; 250/573, 576, 335; 99/493; 426/49, 52, 615

[56] References Cited

U.S. PATENT DOCUMENTS

| | | | |
|---|---|---|---|
| 2,967,450 | 1/1961 | Shields et al. | 250/576 |
| 3,348,409 | 10/1967 | Arthur | 73/19.1 |
| 3,909,136 | 9/1975 | Thomas | 250/573 |
| 3,926,738 | 12/1975 | Wilson | 435/316 |
| 4,270,381 | 6/1981 | Demaray | 73/19.1 |
| 4,293,655 | 10/1981 | Christ et al. | |
| 4,329,433 | 5/1982 | Seebeck et al. | 435/255 |
| 4,371,786 | 2/1983 | Kramer | 250/573 |
| 4,423,670 | 1/1984 | Tenison | 99/275 |
| 4,680,267 | 7/1987 | Eppstein et al. | 435/289 |
| 4,689,304 | 8/1987 | Nelson et al. | 435/291 |
| 4,868,110 | 9/1989 | DesRosier et al. | 435/34 |
| 4,893,935 | 1/1990 | Mandel et al. | 356/436 |
| 4,971,900 | 11/1990 | Ahnell et al. | 435/29 |
| 5,142,969 | 9/1992 | Chun | 435/289 |

*Primary Examiner*—William H. Beisner
*Attorney, Agent, or Firm*—Robert E. Bushnell

[57] ABSTRACT

A pickled vegetables fermentation detector is the sensor for sensing kimchi curing which converts variables depending on the state of kimchi curing into an electric signal and is provided with an air bubble generator, gas collector and detector, in which the inside of the air bubble generator is divided into an upper compartment and lower compartment; gas generated in curing pickled vegetables is collected in the upper compartment to a predetermined quantity and gas is transported to the lower compartment at a predetermined pressure, and the main body of the lower compartment connected to one side of the upper compartment is composed of an air bubble homogeneity device expanded to the lower portion and inserted to a predetermined fluid in the inside of the lower compartment; one wall of a pair of oppositely disposed side walls is thicker than the other, and thickness of the walls is cut off at a predetermined height in the lower wall of both walls and a transparent panel is installed in the proximity of those walls; therefore a groove is formed with a "U"-shaped form, which includes an air bubble detector depending on the kimchi curing state, and is equal in size to the groove, is inserted in the groove. In the main body a light emitting element of a photocoupler including a detector of air bubbles is included on a transparent board formed on the groove of one side wall so that detection of air bubbles is accurately performed depending on generation of air bubbles and on the other side the light receiving element is installed so as to interact with the light emitting element.

16 Claims, 3 Drawing Sheets

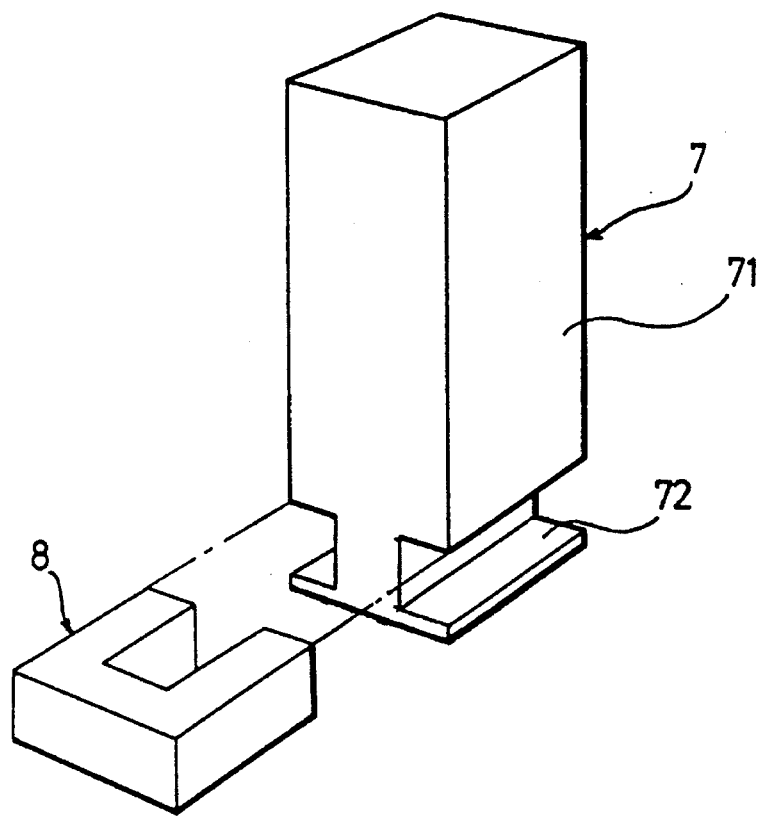
*FIG. 3*
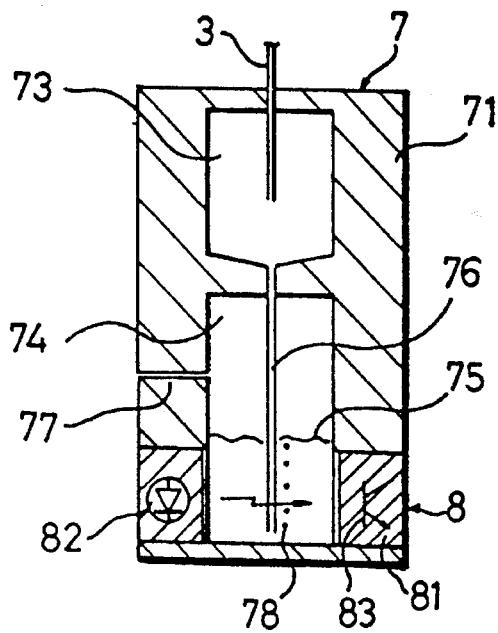 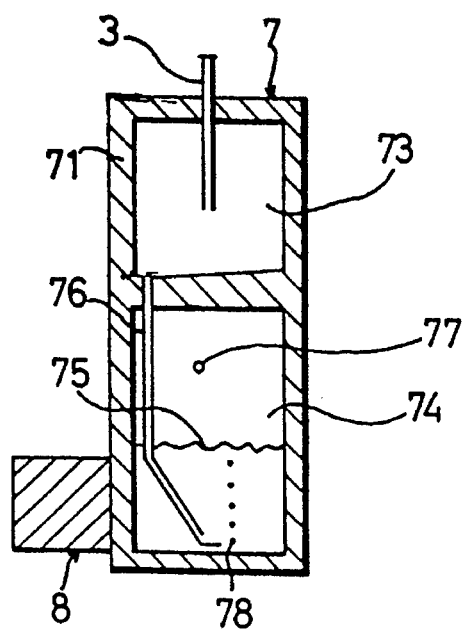
*FIG. 4(a)*      *FIG. 4(b)*

PICKLED VEGETABLES FERMENTATION DETECTING DEVICE

CROSS REFERENCE TO RELATED APPLICATION

This is a continuation of application Ser. No. 07/451,565, filed 18 Dec. 1989 now abandoned.

BACKGROUND OF THE INVENTION

The present invention is related to a pickled vegetables formation detector, particularly to apparatus for detecting the fermentation state of pickled vegetables adapted to detect whether or not picked vegetables have been fermented to an optimum point in a pickled vegetable fermentor such as a refrigerator.

PRIOR ART

Hitherto, according to the passage of time, the fermentation state of pickled vegetables is controlled by varying the temperature of the refrigerator. It has been the problem however, that not only the degree of fermentation is different according to the kind, quantity, seasonings, basic degree, etc. of picked vegetables, but also whether fermentation has been inadequately completed.

Hereupon, according to the results in many studies, it is known that gas is introduced in the fermentation of picked vegetables, that is, carbon dioxide is produced depending on the degree of fermentation of picked vegetables. Gas is slightly produced in the initial stage of fermentation. Depending upon the progress of fermentation however, production of gas is gradually increased, when the fermentation has reached its peak stage, the production of gas was at its maximum and past the peak stage of fermentation, the production of gas gradually decreased. The peak stage of the fermentation, that is, when the gas is most produced, is the most optimum level of the fermentation if we stop the fermentation and store picked vegetables at this stage. This has been described in detail in U.S. Pat. No. 5,142,969 issued 1 Sep. 1992 to Jae-Kun Chung. That is to say, it has been found that kimchi induces generation of gas during the fermentation, and gas is generated as the product of the basic disassimiltationmetabolism and the respiration of the microorganism is dissolved in part in the kimchi solution, but is mostly discharged out of the kimchi solution through the formation of air bubbles.

BRIEF SUMMARY OF THE INVENTION

Consequently it follows that the ratio of a gas in solution to a discharging gas is closely related to the temperature resulting from the formation of kimchi.

Then it has been observed that the generation of air bubbles does not usually occur at the beginning of the fermentation due to the relatively lower concentration of the bacterium; but upon reaching the logarithmic growth phase, air bubbles are significantly increased in size and number and become visible to the naked eye. Therefore, from this viewpoint, the fermentation process of kimchi must be measured, and kimchi fermenting status and environment must be constantly maintained.

Thus, the inventor of a sensor for sensing kimchi curing which converts variables depending on the state of kimchi curing into an electric signal.

This sensor for sensing kimchi curing is similar to the composition of FIG. 1 and FIG. 2 and includes collecting means made of plastic materials in the upperside of a case, and an air bubble homogenium portion made of TEFLON®, a non stick coating etc., not only for receiving, but for rendering uniform the size of bubbles as well as a conveyer tube connected to the lower side of the case inserted by a predetermined height inside of the tube. In one end a photodiode and phototransistor forming a photointerruptor are installed in the case; in the other end of the structure of the case is fixed a reflecting membrane made of silver foil against the photointerruptor.

Therefore, such a sensor collects a gas which is generated in fermenting pickled vegetables using a gas collector, enables the collected gas to be deflated into solution in an air bubble generator so that the gas becomes air bubbles in solution.

And also an air bubble detector, which has a light emitting element and a light receiving element, is installed on the air bubble generator.

Thus, in case no air bubble is generated, the light of the light emitting element flashes on the light receiving element through solution to turn on the light receiving element and, in case an air bubble is generated, the light of the light emitting element is dispersed by the air bubble, so the light does not flash on the light receiving element and the light receiving element is turned off, according to the generation of air bubbles, the light emitting element is alternately turned on and off, and the pulse signal is output depending on the state, from which the sensor detects the state of the fermenting pickled vegetables by this pulse signal.

The increased internal volume due to this construction is troublesome in installation because of being installed in the sealed internal case of the air bubble detector. Particularly, because the homogenitor is installed on the lower end of the case and air bubbles generated thereby float randomly and irregularly. Therefore, the photointerruptor is not able to induce accurate operation.

Accordingly, depending on generation of air bubbles, it is an object of the present invention to provide a detector for fermentation of pickled vegetables in which a detector of air bubble generation is easily installed so that the state of fermentation of pickled vegetables is accurately detected.

Another object of the present invention is to provide a detector of fermentation of pickled vegetables depending on generation of air bubble.

For these and other objects, the present invention includes a gas collector for collecting gas generated in fermentation of pickled vegetables, an air bubble generator making air bubbles with the gas which said gas collector collects, a detector for detecting the curing state of pickled vegetables by air bubbles generated in the air bubble generator according to separated and individually constructed air bubble generator and air bubble generating means, a reflecting surface made of Al is fixed at the predetermined lower location on the air bubble generator, and a transparent surface is installed in the lower wall opposite the reflecting surface.

Also, a device for detecting the generation of air bubbles is suitably arranged in the case on the side of the air bubble generator.

While, in another embodiment of present invention, the inside of the air bubble generator is divided into an upper compartment and lower compartment; gas generated in curing pickled vegetables is collected in the upper compartment to a predetermined quantity and gas is transported to the lower compartment at a predetermined pressure, and the main body of the lower compartment connected to one side of the upper compartment is composed of air bubble homogenator expanded to the lower portion and inserted into a predetermined fluid in the inside of the lower compartment; one of the side walls is thicker than the oppositely positioned side wall, and thickness of the walls is cut off at a predetermined height in the lower wall of both walls and a transparent surface is installed in the proximity of those walls, therefore a groove is formed by cutting off a portion; and, the main body of a "U-shaped" form, which includes an apparatus for detecting air bubbles depending on the kimchi curing state that is equal in size to the groove, is inserted in the groove.

Particularly, in the main body, the light emitting element of the photocoupler has an air bubble detector included on the transparent surface formed on the groove of one side wall so that the detection of air bubbles is accurately performed depending on the generation of air bubbles, and in the other side the light receiving element is installed so as to interact with the light emitting element.

BRIEF DESCRIPTION OF THE DRAWINGS

The above and other objects of the invention will be seen by reference to the description taken in connection with the accompanying drawings, in which:

FIG. 3 is an exploded perspective view showing another embodiment of an air bubble generator and detector of air bubbles according to the curing state of pickled vegetables in the present invention, FIGS. 4(a) and 4(b) are a transverse cross section view and a vertical cross section view of FIG. 3.

DETAIL DESCRIPTION OF THE INVENTION

Figure 1:
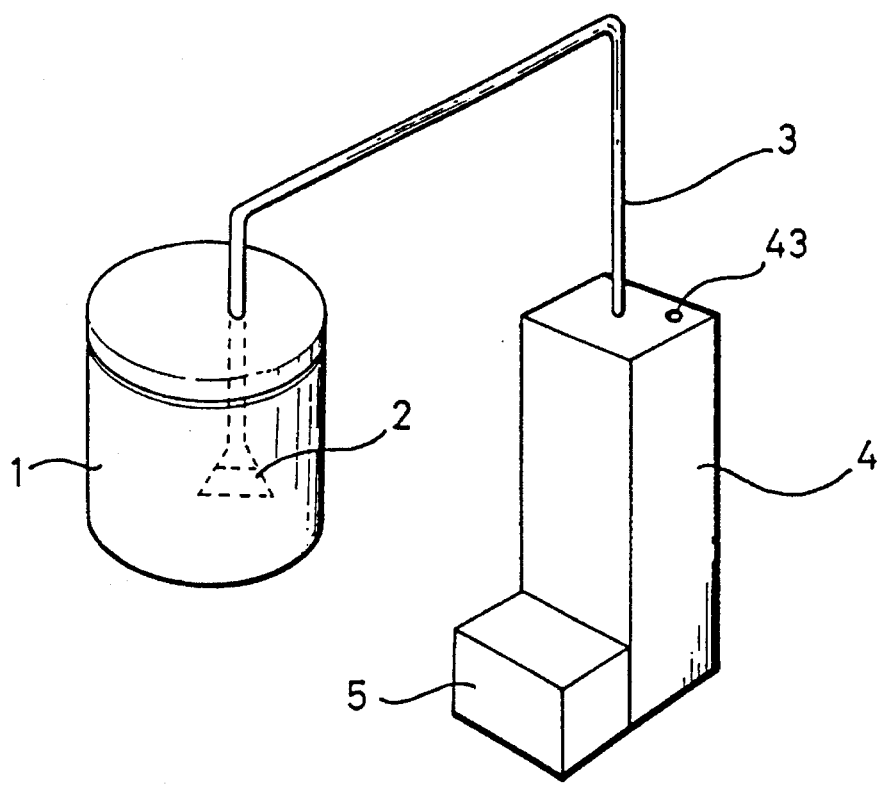
FIG. 1 is a perspective view showing a detector of fermentation according to curing pickled vegetables in the present invention.

FIG. 1 is a vertical view of a detector of fermenting state in the present invention, in which a gas collector 2 having a funnel form is put in the pickled vegetables case 1 and gas generated during the fermentation of pickled vegetables is collected in the gas collector 2. Gas collector 2 is connected to the air bubble generator in which the air bubble generating means is installed through connecting tube 3 composed of homogeneity portion which renders uniform air bubbles.

Figure 2:
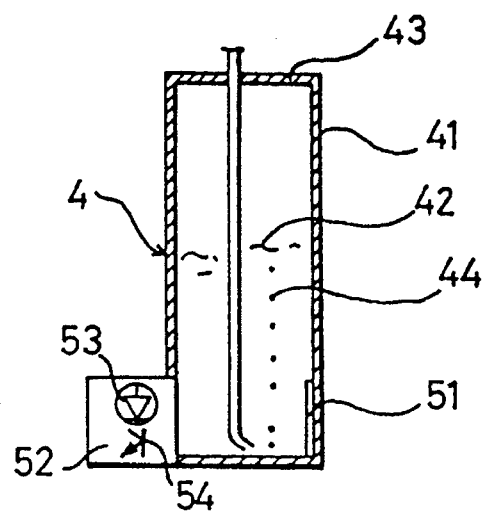
FIG. 2 is a cross section view, shown in detail, of an air bubble generator and detector of air bubbles of FIG. 1.

As shown in FIG. 2, a solution in which carbon dioxide gas generated in pickled vegetables is not dissolved is put in the main body 41 of air bubble generator 4, connecting tube 3 is connected to the lower portion of the solution 42, and there is a gas deflating hole 43 for controlling air pressure of the main body on the upper portion of main body 41. The predetermined portion against hereafter said reflector in the main body 41 is made of a transparent wall on the air bubble generator 4.

Air bubble detector 5 is made so that the reflector 51 made of aluminum (i.e., Al) is installed in the inner lower of main body 41 of air bubble generator, main body 52 of photocoupler which includes light emitting element 53 and light receiving element 54 is installed opposite to reflector 51, so that light from the light emitting element is flashed on the reflector 51 is flashed on light receiving element 53 through solution 42.

In the present invention of such composition, if the pickled vegetables in case 1 ferment and gas is generated, gas is collected by the collector and then is discharged into solution 42 through the connecting tube 3, therefore gas is converted to air bubbles 44 in the solution, the air bubbles 44 rise to the upper portion in the solution 42, and subsequently are deflated to gas exhaust hole 43.

And also, light emitting element 53 of air bubble detector 5 generates light and flashes on reflector 51 through solution 42, light reflected in the reflecting board flashes on the light receiving element 54 and turns on the light receiving element 54. At this time if air bubble 44 is generated, because the light of light emitting element 53 is dispersed, light does not flash on light receiving element 54 and it does not turn off. As the generation of air bubbles 44 increases, the number of times that light receiving element 54 is turned off becomes greater.

FIG. 3 and FIG. 4(a) and FIG. 4(b) are an exploded drawing and cross section drawing showing another embodiment. As shown in these drawings air bubble generator 7 has a concave portion in both the right and left sides of the lower portion of main body 71, the inside of main body 71 is divided with an upper and lower portion and the connecting tube 3 is extended to the middle of upper compartment 73, lower compartment 74 is filled with solution 75 and connecting tube 76 is connected to the lower portion of solution 75 from upper compartment 73 in lower compartment 74, simultaneously a gas discharge hole 77 is drilled on the lower compartment 74.

In the air bubble detector 8, light emitting element 82 and light receiving element 83 are installed in both right side and left side of photocoupler main body 81 having a "U" form, the portion on which light emitting element 82 and light receiving element 83 are installed is inserted into the concave portion 72, so that light of light emitting element 82 flashes on light receiving element 83 through solution 75.

In this alternative embodiment of the present invention, if gas generated in the pickled vegetables is supplied to air bubble generator 7 through connecting tube 3, gas supplied is first discharged into upper compartment 73, gas over the predetermined pressure is discharged from upper compartment 73 to lower portion of solution 75 in lower compartment 74 and, therefore the gas is converted into air bubbles.

And also, light emitting element 82 radiates light, radiated light flashes on light receiving element 83 through solution 75, and if at this time an air bubble is generated, the light of light emitting element 82 is dispersed by air bubble 78 so it does not flash on light receiving element 83; as a consequence of the generation of air bubble 78, light does not flash more frequently on light receiving element 83.

In this point, main body 71 is divided into upper compartment 73 and lower compartment 74 and the reason for such a division is that solution 75 is concentrated within the lower compartment and does not flow in the pickled vegetable case 1 when solution 75 is drawn to and inserted to connecting tube 76 due to low inner pressure of pickled vegetables case 1.

Figure 5:
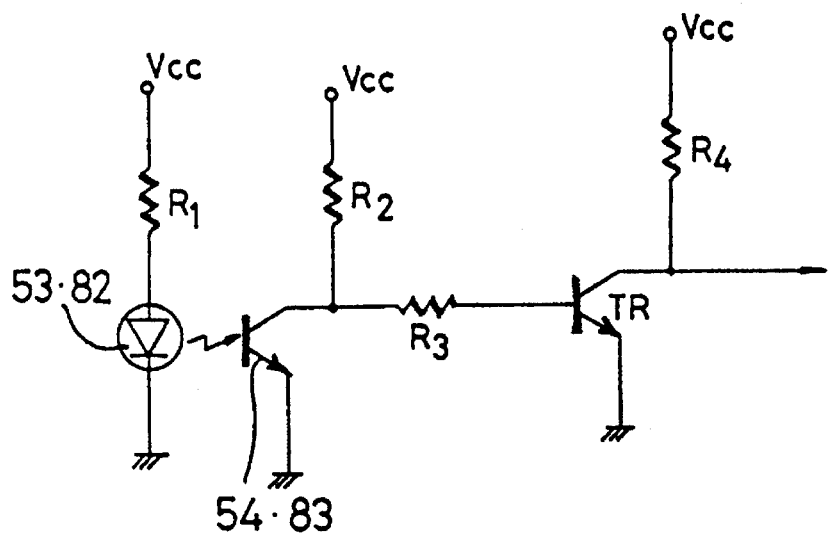
FIG. 5 is a schematic diagram briefly showing detecting operation based on the detector of the present invention.

FIG. 5 is a schematic diagram of a circuit for detecting fermentation. As shown in this drawing, light emitting element 53,82 is connected to the power terminal (Vcc) together with resistor (R) in serial. The collector of light receiving element 54,83 is connected to resistor (R2) and simultaneously to the base of transistor (TR), and the collector of transistor (TR) is connected to resistor (R4) so that any pulse signal output to the connecting point.

In the present invention formed in this way, if power is applied to power terminal (Vcc), light emitting element 53,82 is turned on and radiates light; when air bubble 44,78 is not generated in solution, light from light emitting element 53,82 flashes on light receiving element 54,83; therefore light emitting element 54,83 is turned on, and the transistor is turned off to output a high potential. When air bubble 44,78 is generated, light from light emitting element 53,82 is dispersed by air bubble 44,78, and light receiving element 54,83 is turned off; transistor (TR) is turned on and a low potential is output. This is to say, that depending on generation of air bubble 44,78, transistor (TR) is repeatedly turned on and off and outputs a pulse signal; and the number of air bubbles 44,78 is proportional to the quantity of gas generated.

Figure 6:
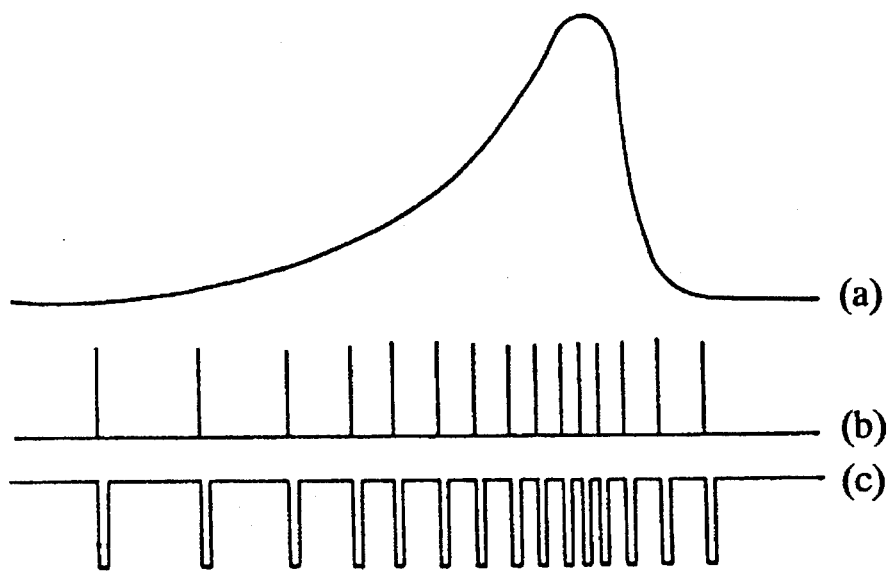
FIG. 6 is a series of waveforms (a), (b) and (c) showing an amount of air bubble and output pulse signal according to the quantity of gas generated during the fermentation of pickled vegetables.

That is to say, as shown in waveform (a) of FIG. 6, if generation of gas increases due to the advancing of fermentation of pickled vegetables, as is shown in (b) of FIG. 6, the number of air bubbles generated is more, as is shown by waveform (c) of FIG. 6 and the number of pulses of low potential is more; therefore fermentation of pickled vegetables is able to be detected by depending on the number of low potential pulses of the signal.

As described in detail thus far, the present invention detects the degree of fermentation by the quantity of gas which is generated according to the fermenting progress of pickled vegetables, therefore have the advantage not only that the degree of fermentation of pickled vegetables is accurately detected but also pickled vegetables are fermented to an optimum level.

What is claimed is:

1. A pickled vegetable fermentation detector, comprising:

means for collecting gas generated during fermentation of pickled vegetables;

a bubble generator providing bubbles with the gas from said gas collecting means, said bubble generator comprising:

a container having an upper portion providing a constant volume accumulating said gas from said gas collecting means under pressure, and a lower portion containing a liquid phase medium; and connecting tube means extending into the liquid phase medium and providing a sole and direct connection between said lower portion of said container and said upper portion of said container, for discharging a series of bubbles of said gas within said liquid phase medium as a function of said volume and said pressure;

detecting means for enabling detection of a state of curing of the pickled vegetables in dependence upon said bubbles generated in said bubble generator, said detecting means comprising a main body separate from said container, said main body partially surrounding said lower portion of said container while separated from said liquid phase medium by said container, said main body including means for making a count of said bubbles discharged from said connecting tube means.

2. The pickled vegetable fermentation detector of claim 1, further comprised of one pair of opposite walls in the lower portion being thicker than an adjoining intermediate pair of opposite walls, and the relatively thicker pair of walls forming a groove providing a transparent wall positioned to receive said main body to enable said detecting means to make an optical count of said bubbles discharged from said connecting tube means.

3. The picked vegetable fermentation detector of claim 2, further comprised of:

said main body having a transparent portion positioned to correspond to said transparent wall, and having a structure in the form of a "U" shaped character with a pair of oppositely disposed, spaced-apart legs, and a light emitting element and light receiving element installed in oppositely disposed legs of the structure.

4. A fermentation detector, comprising:

means for collecting gas generated during fermentation of pickled vegetables;

accumulator means positioned in a housing for providing a first chamber with a constant first volume for receiving said gas from said collecting means, and for accumulating within said first chamber, said gas under a pressure determined by said fermentation;

storing means positioned in said housing below said accumulator means, forming an integral, monolithic structure with said accumulator means, for storing a liquid phase medium within a second volume;

gas discharging means for directly receiving said gas from said accumulator means and discharging immediately within the liquid phase medium as a function of said first volume and said pressure, a series of discrete bubbles of said gas emanating from said first volume; means for enabling said gas from said bubbles to escape from said storing means after said bubbles traverse said liquid phase medium; and means for making a count of said bubbles discharged from said discharging means into the liquid phase medium.

5. The fermentation detector of claim 4, said means for making a count comprising:

means for emitting electromagnetic energy to traverse the liquid phase medium within said storing means; and means for detecting passage of said bubbles through said electromagnetic energy.

6. The fermentation detector of claim 4, comprising:

said storing means comprising a second chamber forming said second volume between a pair of oppositely disposed walls; and said means for making a count comprising:

means for emitting electromagnetic energy to traverse the liquid phase medium between said pair of walls, means positioned in proximity to one wall of said pair of oppositely disposed walls, for reflecting said electromagnetic energy, and means located to receive electromagnetic energy reflected by said reflecting means, for detecting passage of said bubbles through said electromagnetic energy.

7. A fermentation detector, comprised of:

means for collecting gas generated during fermentation of pickled vegetables; accumulator means comprising a first chamber formed in a container with a constant first volume for receiving said gas from said collecting means, and for accumulating within said first chamber said gas under a pressure determined by said fermentation;

storing means comprising a second chamber with a second volume positioned in said container below said first volume, for storing a liquid phase medium;

gas discharging means providing a sole passage between said first chamber and said second chamber, for receiving said gas from said accumulator means and discharging within said liquid phase medium as a function of said pressure determined by said fermentation, a series of discrete bubbles of said gas;

means for enabling said gas from said bubbles to escape from said storing means after said bubbles traverse the liquid phase medium; and means for making a count of said bubbles discharged from said discharging means into the liquid phase medium.

8. The fermentation detector of claim 7, said first chamber comprising a sloped lower surface descending to a region closest to said second chamber.

9. The fermentation detector of claim 7, further comprised of:

said second chamber retaining said liquid phase medium between a first pair of oppositely disposed and spaced-apart walls and a second pair of oppositely disposed and spaced-apart walls interposed between said first pair of walls;

said second pair of walls defining a pair of oppositely disposed grooves; and said means for making a count comprising:
a single, monolithic body having oppositely positioned compartments receivable within said pair of oppositely disposed grooves;
means located within one of said compartments, for emitting electromagnetic energy to traverse the liquid phase medium between said second pair of walls; and
means located within the other one of said compartments, for detecting passage of said bubbles through said electromagnetic energy.

10. The fermentation detector of claim 7, further comprised of:

said second chamber retaining said liquid phase medium between a pair of oppositely disposed and spaced-apart walls having a pair of oppositely disposed grooves positioned within a thickness of said pair of walls; and said means for making a count comprising:
a single, monolithic body having oppositely positioned compartments receivable within said pair of oppositely disposed grooves;
means located within one of said compartments, for emitting electromagnetic energy to traverse the liquid phase medium between said pair of walls; and
means located within the other one of said compartments, for detecting passage of said bubbles through said electromagnetic energy.

11. The fermentation detector of claim 7, wherein said means for making a count comprises:
means located on a side of said second chamber, for emitting electromagnetic energy through the liquid phase medium; and
means located on an opposite side of said second chamber from said emitting means, for detecting passage of said bubbles through said electromagnetic energy.

12. The fermentation detector of claim 7, wherein:
said first chamber comprises a first pair of oppositely disposed and spaced-apart walls and a sloped lower surface descending to a region closest to said second chamber;

said second chamber comprises a second pair of oppositely disposed and spaced-apart walls;

said second pair of walls being thinner than said first pair of walls, to define a pair of oppositely disposed grooves; and said means for making a count comprises:
a body wholly separate and removable from said storing means, having oppositely positioned compartments receivable within said pair of oppositely disposed grooves;
means located within one of said compartments, for emitting electromagnetic energy to traverse the liquid phase medium between said second pair of walls; and
means located within the other one of said compartments, for detecting passage of said bubbles through said electromagnetic energy.

13. A fermentation detector, comprising:

a first chamber of a fixed volume positioned in a container, for collecting gas generated during fermentation of pickled vegetables in a third chamber distinct from said first chamber and said container, said gas within the first chamber providing a pressure within said fixed volume determined by said fermentation;

a second chamber positioned in the container below said first chamber for storing a liquid phase medium in which said gas is insoluble;

means extending from said first chamber and into said second chamber, for discharging within the liquid phase medium as a function of said volume and said pressure, bubbles of said gas from said first chamber; and means for making a count of said bubbles discharged into the liquid phase medium, as said bubbles emanating from said discharging means traverse the liquid phase medium.

14. The detector of claim 13, wherein said means for making a count further comprises:

means for emitting electromagnetic energy to traverse a path of said bubbles as said bubbles traverse the liquid phase medium; and means for detecting passage of said bubbles through said electromagnetic energy.

15. The detector of claim 13, further comprised of:

said first chamber having a sloping floor with a lowest region forming one terminus of said discharging means, said discharging means conducting said gas collected within said first chamber to pass into said second chamber and to be discharged as said bubbles within the liquid phase medium.

16. The detector of claim 15, wherein said means for making a count further comprises:

means for emitting electromagnetic energy to traverse a path of said bubbles as said bubbles traverse the liquid phase medium; and means for detecting passage of said bubbles through said electromagnetic energy.

* * * * *

UNITED STATES PATENT AND TRADEMARK OFFICE
CERTIFICATE OF CORRECTION

PATENT NO. : 5,470,746
DATED : November 28, 1995
INVENTOR(S) : Jae-In Kim

It is certified that error appears in the above-indentified patent and that said Letters Patent is hereby corrected as shown below:

On the title page, item

[75] Inventor: change "Jae I. Kim" to --Jae-In Kim--:

Signed and Sealed this

Sixteenth Day of April, 1996

Attest:

BRUCE LEHMAN

Attesting Officer

Commissioner of Patents and Trademarks